United States Patent

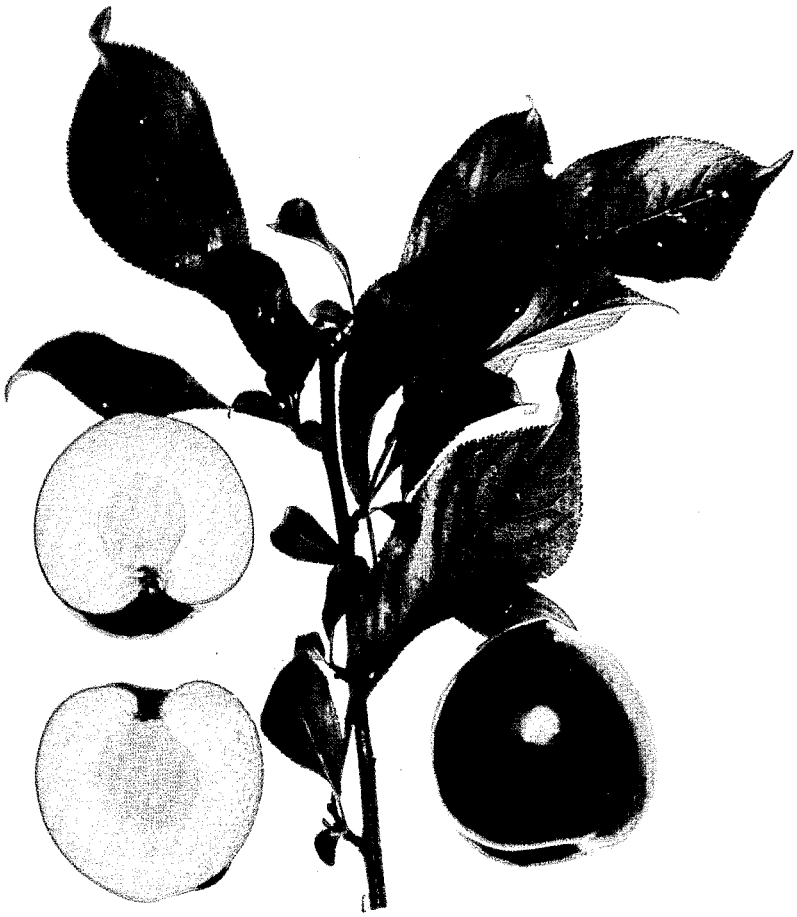

Plant Pat. 3,811

Patented Nov. 25, 1975

3,811

PLUM TREE

Chris Floyd Zaiger, 537 Rosemore Ave., Modesto, Calif. 95351

Filed Jan. 9, 1975, Ser. No. 539,770

Int. Cl. A01h 5/03

U.S. Cl. Plt.—38 1 Claim

ABSTRACT OF THE DISCLOSURE

This variety relates to a plum tree which is of medium to large size, vigorous, medium dense and upright in growth; the tree being a productive and regular bearer of medium, early ripening, clingstone fruit having firm, yellow flesh, and deep violet (16E7 to 17E8) skin color.

ORIGIN OF THE VARIETY

The present variety of plum tree was originated by me, in my experimental orchard, located near Modesto, Stanislaus County, Calif., as a selected seedling from a large number of seedlings obtained from Red Beaut plum seeds (Pat. 2,539) that had resulted from open-pollinated flowers. These seedlings, which were planted and grown under careful observation by me, gave many and varying characteristics, one such seedling which is the present variety, having been considered especially desirable with respect to the fruit, was selected for asexual reproduction and commercialization.

ASEXUAL REPRODUCTION OF THE VARIETY

The present variety of plum tree was asexually reproduced by me, in my said experimental orchard, by budding, and all of such reproductions having run true to the original tree in all respects.

SUMMARY OF THE VARIETY

The present variety of plum tree is of medium to large size, vigorous, medium dense, upright in growth, and a productive and regular bearer of medium size, early ripening, clingstone fruit having firm, yellow flesh and deep violet skin color.

The present variety of plum tree when compared to Red Beaut plum (Pat. 2,539) has a deep violet exterior skin instead of red, has yellow flesh instead of red flesh color, slightly larger in size of fruit, and a slight-apical point on the majority of the fruit. The present variety is a more consistent and regular bearing plum tree than the Red Beaut plum tree.

The present variety of plum tree when compared to Beauty plum (unpatented) matures eight to ten days earlier, is larger in size, and superior in shipping quality.

BRIEF DESCRIPTION OF THE DRAWING

The drawing is an illustration by photographic reproduction in color, of a twig with leaves, one whole fruit, and a cut half with stone remaining in place therein. The skin color is best represented by the ends of the cut halves, the red appearance of the whole fruit being caused by the high reflectance and removal of bloom therefrom.

DESCRIPTION OF THE VARIETY

The botanical details of this new and distinct variety of plum tree—with color definitions (except those in common color terms) referenced to Reinhold Color Atlas by A. Korneruf and J. H. Wanscher—are as follows:

Tree:
- *Size.*—Medium to large.
- *Vigor.*—Vigorous.
- *Growth.*—Upright.

- *Density.*—Medium dense.
- *Shape.*—Vase form.
- *Production.*—Productive.
- *Bearing.*—Regular bearer.

Trunk:
- *Form.*—Medium.
- *Texture.*—Shaggy.

Branches:
- *Size.*—Medium.
- *Texture.*—Medium rough.
- *Color.*—New growth: Reddish brown. Old growth: Brown to grayish brown.

Leaves:
- *Size.*—Medium. Average length—4". Average width—1 3/16".
- *Form.*—Obovate.
- *Thickness.*—Medium.
- *Margin.*—Serrate.
- *Petiole.*—Medium length. Medium thickness.
- *Glands.*—Average number of 2. Range 0 to 5. Usually positioned on base of blade, opposite, small, globose.
- *Color.*—Upper surface—Spinach green—29E6 to 29F8. Lower surface—Grass green—30E7 to 30F8.

Flower buds:
- *Size.*—Medium.
- *Length.*—Medium.

Flowers:
- *Blooming period.*—Date of first bloom: Feb. 27, 1974. Date of full bloom: Mar. 3, 1974. Early to medium as compared to other varieties.
- *Color.*—White.

Fruit:
- *Maturity when described.*—Hard Ripe.
- *Date of first picking.*—June 4, 1974.
- *Date of last picking.*—June 11, 1974.
- *Size.*—Slightly variable. Average diameter axially 2 1/16". Average transversely in suture plane 1 15/16".
- *Form.*—Uniform. Globose.
- *Suture.*—Shallow.
- *Cavity.*—Rounded. Average depth—1/4". Average breadth—5/8".
- *Base.*—Rounded.
- *Apex.*—Short. Varied from rounded to slightly pointed, most of the fruit slightly pointed.
- *Stem.*—Average length—5/8". Average width—1/16". Color: Olive yellow (3D6).

Skin:
- *Thickness.*—Medium.
- *Texture.*—Medium.
- *Tendency to crack.*—None in dry seasons.
- *Down.*—Wanting.
- *Color.*—Deep violet (16E7 to 17E8).

Flesh:
- *Texture.*—Firm. Fine. Meaty.
- *Fibers.*—Few. Tender.
- *Ripens.*—Evenly.
- *Flavor.*—Subacid to slightly acid.
- *Eating quality.*—Good.
- *Color.*—Yellow (4A7 to 5A6).

Stone:
- *Type.*—Clingstone—adheres to flesh over entire surface.
- *Size.*—Medium to small. Average length—3/4". Average breadth—11/16".
- *Color.*—Apricot yellow (5B6).

Use: Market.

Keeping quality: Very good.

Shipping quality: Very good.

The plum tree and its fruit herein described may vary in slight detail due to climatic and soil conditions under which the variety may be grown; the present description being of the variety as grown near Modesto, Calif.

I claim:

1. A new and distinct variety of plum tree, substantially as illustrated and described, which bears medium-size, clingstone fruit with firm, yellow flesh and deep violet skin, in contrast with its seed parent, Red Beaut, which bears fruit less productively and regularly, which fruit has a red skin, yellow flesh, and is smaller.

No references cited.

ROBERT E. BAGWILL, Primary Examiner